United States Patent [19]

Hughes

[11] Patent Number: 5,702,645
[45] Date of Patent: Dec. 30, 1997

[54] PHOTOCHROMIC CHROMENE DERIVATIVES

[75] Inventor: Frank J. Hughes, Edina, Minn.

[73] Assignee: Vision-Ease Lens, Inc., Brooklyn Center, Minn.

[21] Appl. No.: 550,033

[22] Filed: Oct. 30, 1995

[51] Int. Cl.$^6$ ................................. C07D 493/04
[52] U.S. Cl. .................. 252/586; 351/163; 524/109; 524/110; 544/150; 544/378; 546/197; 549/387
[58] Field of Search ............... 549/387; 544/150, 544/378; 546/197; 351/163; 524/109, 110; 252/586

[56] References Cited

U.S. PATENT DOCUMENTS

| | | | |
|---|---|---|---|
| 3,567,605 | 3/1971 | Becker | 204/158 |
| 4,685,783 | 8/1987 | Heller et al. | 530/161 |
| 4,818,096 | 4/1989 | Heller et al. | 351/163 |
| 4,826,977 | 5/1989 | Heller et al. | 544/70 |
| 4,882,438 | 11/1989 | Tanaka et al. | 548/407 |
| 4,931,221 | 6/1990 | Heller | 252/586 |
| 4,990,287 | 2/1991 | Bennion et al. | 252/586 |
| 5,055,576 | 10/1991 | Castaldi et al. | 540/543 |
| 5,106,998 | 4/1992 | Tanaka et al. | 549/331 |
| 5,238,981 | 8/1993 | Knowles | 524/110 |
| 5,242,624 | 9/1993 | Malatesta et al. | 252/586 |
| 5,244,602 | 9/1993 | Van Gemert | 252/589 |
| 5,274,132 | 12/1993 | VanGemert | 549/389 |

OTHER PUBLICATIONS

Dean et al., CA 110:135109 (1989).
Sadykov et al., CA 110:23409 (1989).
Venugopalan et al., CA 102:220767 (1985).
Liska, CA 78:11445 (1973).
Besace et al., CA 75:88236 (1971).
Besace, Yvon, Israël Marszak, and Jocelyne Maisse; Synthesis and Applications of Monoaryl Ethers of Butynediol; *Bull. Soc. Chim. Fr.*; No. 6; pp. 2275–2279; (1971).
Dean, Francis M., Steven N. France and Ulku Oyman; Cation Radicals in the Bromination of Benzodipyran Derivatives; *Tetrahedron*; vol. 44, No. 15; pp. 4857–4862; (1988).
Liska, Kenneth J.; Preparation and Antitumor Properties of Analogs of Acronycine; *Journal of Medicinal Chemistry*; vol. 15, No. 11; pp. 1177–1179; (1972).
Sadykov, T., K.B. Erzhanov, M.B. Basymbekov, and S.D. Praliev; Hydration of o–, m–, and p–bit (Propynyloxy) Benzenes and Their Glycols; *Ivz. Akad. Nauk Kaz. SSR, Ser. Khim*; No. 1; pp. 63–67; (1988).
Venugopalan, Bindumadhavan and Kalpattu Kuppuswamy Balasubramanian; Studies on Claisen Rearrangement of Bis–Propargyl Ethers—Synthesis of Naphthodipyrans, Naphthodifurans and Naphthofuropyrans; *Heterocycles*; vol. 23, No. 1; pp. 81–92; (1985).

*Primary Examiner*—Johann Richter
*Assistant Examiner*—Laura L. Stockton
*Attorney, Agent, or Firm*—Kinney & Lange, P.A.

[57] ABSTRACT

Described herein are photochromic compounds or a structural isomer of the photochromic compound, the photochromic compounds represented by the formula:

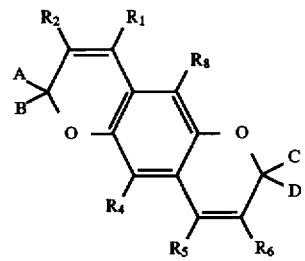

wherein $R_1$, $R_2$, $R_4$, $R_5$, $R_6$, $R_8$, A, B, C, and D are each selected from the group consisting essentially of hydrogen, a stable organic radical, a heterocyclic group, halogen, a nitrogen-substituted radical, and a nitrogen-substituted ring radical.

20 Claims, No Drawings

PHOTOCHROMIC CHROMENE DERIVATIVES

BACKGROUND OF THE INVENTION

The present invention generally relates to chromene derivatives and to compositions that include chromene derivatives. More specifically, the present invention relates to photochromic chromene derivatives and to compositions that include photochromic chromene derivatives.

Photochromism generally concerns the ability of a compound to reversibly change color under different light conditions. One particular type of photochromic phenomenon concerns the reversible change in color of a photochromic compound from an original color to a different color when the compound is exposed to a source of ultraviolet radiation, such as solar radiation or light radiated from a mercury or xenon lamp. Of course, the original color may in fact be a colorless state. The photochromic compound fades to the original color, or the colorless state, within a period of time after the compound is isolated from the ultraviolet radiation, such as by placing the compound in a dark room.

Each particular photochromic compound has a particular set of definitive characteristics. There is a need for the invention and development of additional photochromic compounds, since the existing photochromic compounds do not satisfactorily address consumer desires for articles incorporating photochromic compounds having particular characteristics.

One characteristic of a particular photochromic compound is the ability, or inability, to reversibly change color. A number of other characteristics relate to the color change characteristic. Some of these other characteristics include the color the compound changes to; the attributes of the color, such as the hue, lightness, and saturation of the color; the rate at which the color change occurs; and the rate at which the compound reverts to the original color from the different color, if the color change is reversible. A number of variables may affect these color and rate characteristics, including the temperature of the compound, whether or not the compound is incorporated into a matrix or a solution, the characteristics of the matrix or solution, and the light conditions the compound is exposed to, including the presence or absence of light, the wavelength of the light, and the intensity of the light. The light conditions also impact another characteristic relating to the color change characteristic, the effect of mixtures of light wavelengths of the same or different intensities on the color the compound changes to and on the stability of the color the compound changes to.

Various products, including optical lenses, incorporate the principal of photochromism. For example, photochromic compounds, such as naphthopyrans, are incorporated into matrices, such as plastic ophthalmic lenses, to effect color changes in the lenses when the lenses are exposed to particular lighting conditions. Additionally, different photochromic compounds may be blended to create a color effect that is different from the respective color effects of the individual photochromic compounds. As an example, a first photochromic compound that turns orange or red when activated by light and a second photochromic compound that turns blue when activated by light may be blended to form a photochromic mixture that produces a shade of gray when activated by light.

Several types of photochromic compounds have been reported which exhibit changes in color when exposed to ultraviolet light. One particular class of photochromic compounds includes chromene derivatives, such as the 3,3-disubstituted naphthopyrans. One specific group of 3,3-disubstituted naphthopyrans includes the 3H-naphtho[2,1b]pyrans. The color response of the 3H-naphtho[2,1b]pyrans to ultraviolet light extends to purple, red, orange or yellow, depending upon the composition and structure of the particular 3H-naphtho[2,1b]pyran and the ambient conditions, such as temperature and light conditions. A general expression of the 3H-naphtho[2,1b]pyrans is provided in graphical formula I:

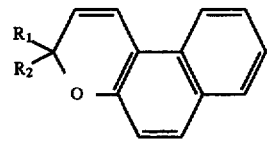

where $R_1$ and $R_2$ are substituents attached to the pyran ring at the position indicated.

Several photochromic compounds are described in U.S. Pat. No. 3,567,605 to Becker. The Becker patent describes various chromenes and chromene derivatives that are photochromic at relatively low temperatures, such as temperatures below about −40° C. These chromene derivatives are not useful for incorporation into ophthalmic lenses since ophthalmic lenses are typically worn at temperatures much warmer than −40° C. The Becker patent also describes chromenes and chromene derivatives that are photochromic at room temperature, such as diphenyl-3H-naphtho[2,1b]pyran, where $R_1$ and $R_2$ of formula I are each unsubstituted phenyl groups.

Additional photochromic compounds are described in U.S. Pat. No. 4,931,221 to Heller et al. One type of photochromic compound described in Heller generally has the form of graphical formula I with $R_1$ and $R_2$ being cyclopropyl radicals and with any of various substituents included on the naphtho portion of the naphthopyran rings. Heller reports a larger bathochromic shift in the visible spectrum of 3H-naphtho[2,1b]pyrans that include the cyclopropyl radicals, as compared to 3H-naphtho[2,1b]pyrans that include alkyl groups or a spirocycloalkyl group in place of the cyclopropyl radicals.

Other photochromic compounds are described in U.S. Pat. No. 5,066,818 to Gemert et al. One photochromic compound class described in Gemert generally meets graphical formula I with one of $R_1$ and $R_2$ being a substituted phenyl radical, with one of $R_1$ and $R_2$ being either a substituted or unsubstituted phenyl radical, and with various substituents included on the naphtho portion of the naphthopyran rings. Gemert lists various non-aryl groups as potential substituents of the phenyl radicals of $R_1$ and $R_2$. Gemert reports a range of decolorization rates associated with the 3H-naphtho[2,1b]pyrans that include the phenyl radicals as $R_1$ and $R_2$.

Additional photochromic compounds are described in U.S. Pat. No. 5,106,998 to Tanaka et al. Tanaka describes compounds in which $R_1$ and $R_2$ of graphical formula I are alkyl groups. Tanaka reports several fade times and maximum absorption wavelengths associated with various 3H-naphtho[2,1b]pyrans that include the alkyl radicals as $R_1$ and $R_2$ in formula I.

U.S. Pat. No. 5,238,981 to Knowles teaches a 3H-naphtho[2,1b]pyran compound in which $R_1$ and $R_2$ of graphical formula I are each selected from a group of organic radicals that includes phenyl and naphthyl. The organic radicals placed at $R_1$ and $R_2$ are either substituted or unsubstituted. Potential substituents of substituted organic radicals placed at $R_1$ and $R_2$, provided that one of the organic radicals placed at $R_1$ and $R_2$ is a phenyl group, include various non-aryl groups. Various potential substitutions on the naphtho portion of the naphthopyran ring are taught, including an 8-methoxy substitution. Knowles states that the number eight carbon atom substitutions, such as the 8-methoxy substitution, cause a bathochromic shift in the visible spectrum associated with activated forms of the 3H-naphtho[2,1b]pyrans and in the ultraviolet spectrum of unactivated forms of the 3H-naphtho[2,1b]pyrans.

Additional photochromic compounds are described in U.S. Pat. No. 5,244,602 to Van Gemert. Van Gemert describes 3H-naphtho[2,1b]pyrans in which $R_1$ and $R_2$ of graphical formula I are each phenyl, naphthyl, various heterocyclic groups, and certain non-aryl groups. Van Gemert also discusses substitution of various non-aryl substituents into any phenyl, naphthyl, heterocyclic, and non-aryl groups placed at $R_1$ and $R_2$. Van Gemert also states that certain substitutions at the number 5 carbon on the naphtho ring causes a bathochromic shift of the absorption maximum of the 3H-naphtho[2,1b]pyrans.

U.S. Pat. No. 5,274,132 to Van Gemert describes certain 3H-naphtho[2,1b]pyrans in which $R_1$ of graphical formula I is a phenyl group, a naphthyl group, a furyl group, or a thienyl group and in which $R_2$ of graphical formula I is an arylalkenyl radical. Van Gemert describes a bathochromic shift associated with the 3H-naphtho[2,1b]pyrans that include the arylalkenyl radical, relative to certain other naphthopyrans disclosed in U.S. Pat. No. 3,567,605.

Other photochromic compounds are described in U.S. Pat. No. 4,685,783 to Heller et al., U.S. Pat. No. 4,882,438 to Tanaka et al., U.S. Pat. No. 5,055,576 to Castaldi, and U.S. Pat. No. 5,242,624 to Malatesta et al. Other photochromic compounds that are derivatives of chromene are described in U.S. Pat. No. 4,818,096 to Heller et al., U.S. Pat. No. 4,826,977 to Heller et al., and U.S. Pat. No. 4,990,287 to Bennion et al.

Though a number of photochromic compounds with particular characteristics have been identified, the characteristics of any particular one of these compounds do not meet all demands of current consumers. Thus, there is a need for the invention and development of additional photochromic compounds that address changing consumer desires for articles incorporating photochromic compounds having particular characteristics.

SUMMARY OF THE INVENTION

The present invention includes a photochromic compound represented by the formula:

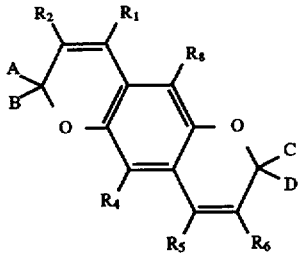

wherein $R_1$, $R_2$, $R_4$, $R_5$, $R_6$, $R_8$, A, B, C, and D are each selected from the group consisting essentially of hydrogen, a stable organic radical, a heterocyclic group, halogen, a nitrogen-substituted radical, and a nitrogen-substituted ring radical. The present invention further includes a chromene derivative and a photochromic product.

DETAILED DESCRIPTION OF THE PREFERRED EMBODIMENTS

Novel photochromic compounds that are derivatives of chromene have been discovered which selectively absorb high wavelength, visible spectrum light at room temperature when activated by ultraviolet light. When activated, the photochromic compounds change from an original color to a different color and exhibit deep coloring ranging from orange to reddish-orange to purple, for a particular photochromic compound. On activation, the novel photochromic compounds display colors that are capable of being blended with blue-appearing photochromic compounds to form photochromic blends that exhibit remarkably pleasing gray colors when the blends are activated by ultraviolet radiation.

Also, a photochromic reaction mixture or product that includes two or more structural isomers of the inventive photochromic compound is believed to result on formation of a particular one of the inventive photochromic compounds. On activation, each photochromic reaction mixture or product exhibits a pair of maximum wavelength absorption peaks that combine to selectively produce pleasing colors ranging from gray to brownish gray for a particular photochromic reaction mixture or product. Besides pleasing coloring characteristics, the novel photochromic compounds and the photochromic reaction mixtures or products have other desirable characteristics, such as good color stability on activation and acceptable fade times for reversion to the original color from the different color that make the photochromic compounds and mixtures useful for incorporation into a variety of matrices for making photochromic articles.

Novel chromene derivatives of the present invention that are useful as photochromic compounds may be represented by graphic formula II as follows:

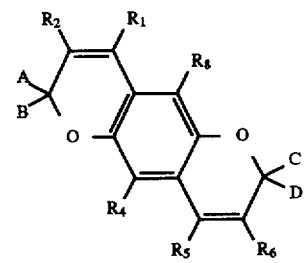

For purposes of the present application, including the description and the claims, it is to be understood that graphical formula II includes all structural isomers of the chromene derivatives represented by graphical formula II.

A variety of elements, groups, and radicals may be included in the photochromic compound of graphic formula II. For example, in graphic formula II, any of the positions represented by $R_1$, $R_2$, $R_4$, $R_5$, $R_6$, $R_8$, A, B, C, and D may be individually selected from any of the following: hydrogen; any stable organic radical, such as alkyl, alkoxy, unsubstituted or substituted phenyl, unsubstituted or substituted phenoxy, naphthyl, naphthoxy, cycloalkyl, furyl, alkoyl, alkoyloxy, aroyl, or aroyloxy; any heterocyclic group; halogen; any nitrogen-substituted radical, such as amino, dialkyl amino, or nitro; and any nitrogen-substituted ring radical, such as morpholino, piperidino, or piperazino.

Preferably, in graphic formula II, the positions represented by $R_1$, $R_2$, $R_4$, $R_5$, $R_6$, and $R_8$ and the positions represented by A, B, C, and D are filled with different groups, radicals or elements. For example, any of the positions represented by $R_1$, $R_2$, $R_4$, $R_5$, $R_6$, and $R_8$ may be individually selected from any of the following: hydrogen; a first stable organic radical, such as alkyl, alkoxy, unsubstituted or substituted phenyl, unsubstituted or substituted phenoxy, naphthyl, naphthoxy, cycloalkyl, furyl, alkoyl, alkoyloxy, aroyl, or aroyloxy; a first heterocyclic group; halogen; a first nitrogen-substituted radical, such as amino, dialkyl amino, or nitro; and a first nitrogen-substituted ring radical, such as morpholino, piperidino, or piperazino. Also, any of the positions represented by A, B, C, and D may be individually selected from any of the following: a second stable organic radical, such as alkyl, alkoxy, unsubstituted or substituted phenyl, unsubstituted or substituted phenoxy, naphthyl, naphthoxy, cycloalkyl, furyl, alkoyl, alkoyloxy, aroyl, or aroyloxy; a second heterocyclic group; halogen; a second nitrogen-substituted radical, such as amino, dialkyl amino, or nitro; and a second nitrogen-substituted ring radical, such as morpholino, piperidino, or piperazino.

More preferably, the positions in graphic formula II represented by A, B, C, and D are individually filled with any stable substituted or unsubstituted organic radical, such as alkyl, alkoxy, phenyl, naphthyl, cycloalkyl, furyl, alkoyl, alkoyloxy, aroyl, or aroyloxy. Any substituents of the stable organic radical(s) filling the positions represented by A, B, C, and D may be selected from the following: hydrogen; the second stable organic radical, such as alkyl, alkoxy, unsubstituted or substituted phenyl, unsubstituted or substituted phenoxy, naphthyl, naphthoxy, cycloalkyl, furyl, alkoyl, alkoyloxy, aroyl, or aroyloxy; the second heterocyclic group; halogen; the second nitrogen-substituted radical, such as amino, dialkyl amino, or nitro; and the second nitrogen-substituted ring radical, such as morpholino, piperidino, or piperazino.

Still more preferably, the positions in graphic formula II represented by A, B, C, and D may be individually filled with any of the following: an unsubstituted monovalent aromatic radical and a substituted monovalent aromatic radical. Any substituents of any substituted monovalent aromatic radical or radicals may be selected from the following: hydrogen; the second stable organic radical, such as alkyl, alkoxy, unsubstituted or substituted phenyl, unsubstituted or substituted phenoxy, naphthyl, naphthoxy, cycloalkyl, furyl, alkoyl, alkoyloxy, aroyl, or aroyloxy; the second heterocyclic group; halogen; the second nitrogen-substituted radical, such as amino, dialkyl amino, or nitro; and the second nitrogen-substituted ring radical, such as morpholino, piperidino, or piperazino. Preferably any substituents of any substituted aromatic radical or radicals are selected from alkyl, alkoxy, phenyl, naphthyl, cycloalkyl, furyl, alkoyl, alkoyloxy, aroyl, or aroyloxy.

The photochromic compounds represented by graphic formula II are derivatives of 3,3-aryl-di-substituted-aryl chromenes. These photochromic compounds exhibit a surprising and highly desirable bathochromic shift of the maximum absorption wavelength when activated by ultraviolet light. The bathochromic shift exhibited by the inventive photochromic compounds provide photochromic species which turn deep shades of orange, reddish-orange or purple when activated by a source of ultraviolet radiation, such as solar radiation or light radiated from a mercury or xenon lamp, at temperatures typically encountered by consumers, such as temperatures ranging from about 0° F. to about 100° F.

It has been found desirable to produce photochromic compounds with maximum activated wavelengths of absorption approaching and even exceeding 500 nanometers. Photochromic compounds with maximum activated wavelengths of absorption near or above 500 nanometers change from original states of color to deep shades of orange, reddish-orange or red when activated by ultraviolet light. The colored forms of the activated photochromic compounds fade to the original, unactivated colored states at ambient temperatures when isolated from the ultraviolet light. Photochromic compounds that turn deep shades of orange, reddish orange, or red when activated are hereinafter referred to as "intense photochromes" for purposes of this disclosure only.

The inventive chromene derivatives represented by graphical equation II, especially the intense photochromes, exhibit a deep color and a larger bathochromic shift in the visible spectrum, when activated by ultraviolet light, as compared to current photochromic compounds, such as current naphthopyrans. Indeed, at least some of the inventive chromene derivatives represented by graphical equation II, especially the intense photochromes, have maximum activated wavelengths that exceed 500 nanometers and exhibit deep shades of orange, reddish orange, or purple when activated. At least one of the inventive chromene derivatives represented by graphical equation II surprisingly attains a maximum activated wavelength of 560 nanometers.

Besides the desirable maximum absorption wavelengths, the inventive photochromic compounds represented by graphical equation II have other desirable photochromic characteristics. For example, the inventive photochromic compounds have desirable activated coloring attributes, such as the hue, lightness, and saturation of the color the individual compounds change to. Also, the inventive photochromic compounds change from the original color state to the activated color at desirable rates when exposed to ultraviolet light. Additionally, the inventive photochromic compounds have desirable fade rates so that the photochromic compounds revert to the original color state from the activated color at desirable rates when the photochromic compounds are isolated from the ultraviolet light. Also, when activated by ultraviolet light, the aforementioned desirable coloring characteristics are stable and are not deleteriously affected by light having wavelengths different from the wavelength of the activating source. Furthermore, each inventive photochromic compound has a distinct set of definitive photochromic characteristics that lends each of the inventive photochromic compounds particularly suited to particular photochromic applications, as compared to existing photochromic compounds.

One suitable method of preparing photochromic compounds having the structure of graphic formula II involves reacting a suitable ketone precursor with a metal salt of an alkyne to make an intermediate. The intermediate is then reacted with either an unsubstituted fused heterocycle or a substituted fused heterocycle in the presence of a catalyst. The resultant material is then purified by recrystallization, column chromatography, or a combination of recrystallization and column chromatography.

Some examples of suitable ketone precursors include 4-benzoyl biphenyl, 3,4-dimethylbenzophenone, 3-chlorobenzophenone, 4,4'-dimethoxybenzophenone and benzophenone. The metal salt of the alkyne is preferably lithium acetylide and the organic solvent is preferably tetrahydrofuran. Some examples of fused heterocycles include hydroquinone, methylhydroquinone, and phenylhydroquinone. The catalyst is preferably a catalytic amount of p-toluenesulfonic acid.

Some examples of chromene derivatives of the present invention, consistent with graphic formula II, include the photochromic compound that may be represented by graphic formulas III, IV, and V below:

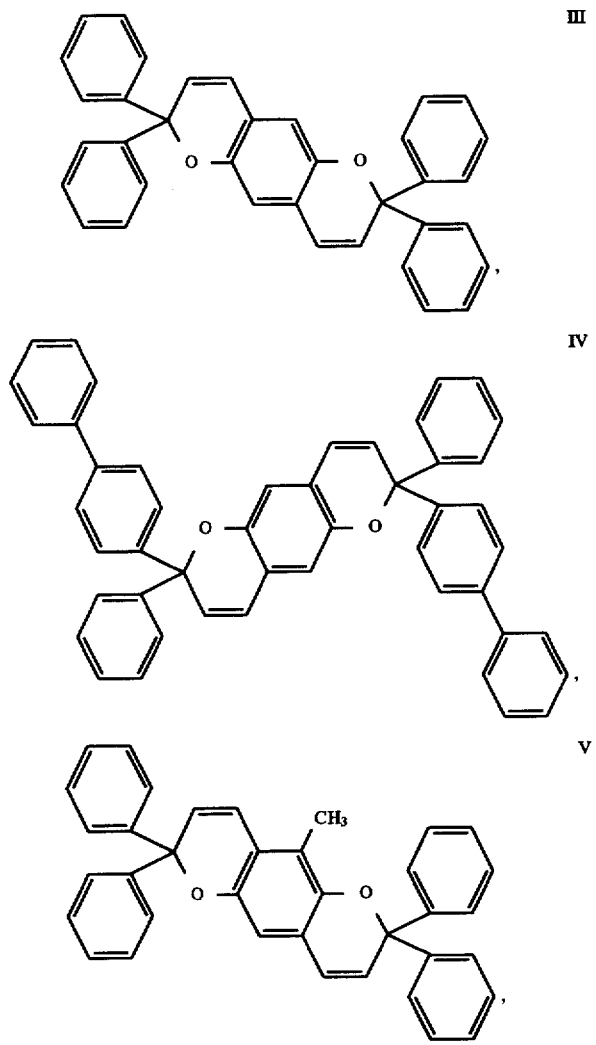

It is to be understood that the chromene derivatives depicted in graphical formulas III, IV, and V include all structural isomers of the respective chromene derivatives represented by graphical formulas III, IV, and V. The exemplary methods set forth later in this application for producing the inventive chromene derivatives represented by graphical formula II form photochromic reaction products. Each of photochromic reaction products are believed to include a particular photochromic compound represented by graphical formula II, as well as, at least one structural isomer of the particular photochromic compound formed by the method.

When dissolved in chloroform, the photochromic reaction products unexpectedly exhibit two maximum activated wavelengths of absorption, as set forth in Table 1 below, when irradiated with ultraviolet light. Additionally, when activated by ultraviolet light, the photochromic reaction products that occur on formation of the photochromic compounds of graphical formula II exhibit select shades of color in the visible light spectrum ranging from brownish gray to gray for particular photochromic reaction products. Therefore, when a gray-turning photochromic compound is desired, the photochromic reaction product of the present invention, such as the photochromic reaction product that includes the photochromic compound of graphical formula III and the associated photochromic isomer(s), the photochromic reaction product that includes the photochromic compound of graphical formula IV and the associated photochromic isomer(s), or the photochromic reaction product that includes the photochromic compound of graphical formula V and the associated photochromic isomer(s), may be directly incorporated into the photochromic article without first blending the photochromic reaction product with another photochromic compound, such as a substituted spiroindolino naphthoxazine.

The intense photochromes of the present invention may be blended with one or more other photochromic compounds of different maximum activation wavelengths of absorption from that of the inventive intense photochromes to make photochromic blends. Preferably, the other photochromic compounds turn colors other than orange, reddish orange and purple when activated with ultraviolet light. In one embodiment, one or more of the inventive intense photochromes may be blended with another photochromic compound which has a different maximum activation wavelength of absorption and which turns blue when activated with ultraviolet light to make the photochromic blend. Alternatively, the photochromic reaction products that includes the photochromic compounds and associated photochromic isomers may be used alone to attain the grayish color upon exposure to ultraviolet light. The photochromic blends and the photochromic reaction products may be desirably applied to or incorporated within substrates, such as conventional synthetic plastic materials often used for optical elements.

The photochromic compounds represented by graphic formula II may be used in many applications of plastic substrates. For example, compounds represented by graphic formula II may be incorporated into a host material that is applied to an article. Also, compounds represented by graphic formula II may be combined with host material that is used to make the article. Additionally, compositions that contain one or more of the photochromic compounds represented by graphic formula II, such as the previously mentioned photo-chromic blends or the photochromic reaction products, may be incorporated into the host material. The combination of the composition and host material, as already noted, may be applied to the article or may be used to make the article. Compounds represented by graphic formula II and compositions containing one or more compounds represented by graphic formula II may be coated onto the host material, the article, or other suitable substrate. Furthermore, photochromic reaction products that include the particular photochromic compound and associated photochromic isomer of the particular photochromic compound may be coated onto the host material, the article, or other suitable substrate.

Polymerized organic materials, such as synthetic polymerized plastic often used to make optical elements, are examples of the host material. Examples of the article include optical elements, such as plano and ophthalmic lenses. Non-exhaustive illustrations of suitable synthetic polymerized plastics suitable for use as the host material include polyacrylate, polycarbonate, polyvinyl alcohol, polyvinyl acetate, polyvinyl chloride, polyurethane, cellulose ester and bis-polyol (allyl carbonate) monomer-based polymer.

As used in this disclosure, including the description and the claims, the term bis-polyol (allyl carbonate) monomer and similar phrases are intended to mean and include the named monomer or prepolymer and any related monomer series contained therein. Some non-limiting examples of bis-polyol (allyl carbonate) monomers include ethylene glycol bis(allyl carbonate), di-ethylene glycol bis(2-methylallyl carbonate), diethylene glycol bis(allyl carbonate), propylene glycol bis(2-ethylallyl carbonate), 1-3-propanediol bis(allyl carbonate), 1,3-butanediol bis(allyl carbonate), 1,4-butanediol bis(2,bromoallyl carbonate), dipropylene glycol bis(allyl carbonate), trimethylene glycol bis(2-ethylallyl carbonate), pentamethylene glycol bis(allyl carbonate), and isopropylidene bisphenol bis(allyl carbonate).

The amount of a particular one of the compounds represented by graphic formula II, or a particular composition containing one of the compounds represented by graphic formula II, that is incorporated into the host material or the coating material is defined, for purposes of this disclosure, as the photochromic amount. The photochromic amount is not critical, provided that a sufficient amount to produce a photochromic effect perceptible to the human eye is used. The photochromic amount often depends on the desired intensity of the color on activation of the particular inventive photochromic compound and on the method of incorporation or application of the particular inventive photochromic compound. Typically, the photochromic amount incorporated into or applied to the host material or incorporated into the coating material rages from about 0.01 to about 20 percent by weight, based on the weight of the host material or the weight of the coating material, as applicable.

The present invention is more particularly described in the following examples which are intended as illustrations only since numerous modifications and variations within the scope of the general formulation will be apparent to those skilled in the art.

EXAMPLE 1

Step 1

Five grams of benzophenone were placed together with five grams of lithium acetylide in 250 milliliters of tetrahydrofuran and stirred for 72 hours. The resultant mixture was poured over ice and diluted with water to form an organic layer and an aqueous layer. The organic layer was separated from the aqueous layer and dried with anhydrous sodium sulfate. The dried organic layer was evaporated to obtain a solid material. The solid material was triturated with acetone. The triturated material was dissolved in a solvent and the solvent solution was cooled to yield a recrystallized compound. Nuclear magnetic resonance (NMR) spectroscopy showed the resultant material to be a relatively pure propargyl alcohol.

Step 2

Two grams of the propargyl alcohol obtained in Step 1 were mixed with 1.00 grams of hydroquinone in 200 milliliters of benzene. Twenty milligrams of p-toluenesulfonic acid were then added and the mixture was stirred under reflux for 8 hours. The resultant mixture was cooled and washed with 10% aqueous sodium hydroxide. The organic solvent (benzene) was removed using a rotary evaporator. The resulting material was dissolved in hexane and the resulting hexane solution was cooled to yield a recrystallized reaction product. The recrystallized reaction product was shown by nuclear magnetic resonance (NMR) spectroscopy to contain the following photochromic compound:

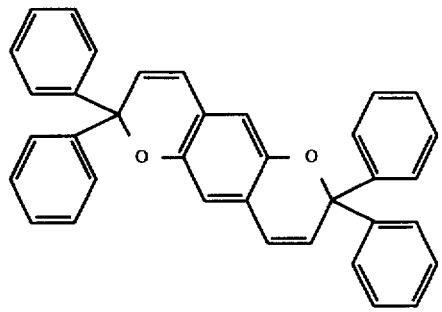

It is also believed that the recrystallized reaction product of Step 2 also contained at least one photochromic structural isomer of this photochromic compound. Ultraviolet visible spectroscopy indicated that the recrystallized reaction product of Step 2, when dissolved in chloroform and irradiated with ultraviolet light of 350 nanometer wavelength, had two maximum wavelengths of absorption at 438 nanometers and at 530 nanometers. Additionally, the irradiated product had a visually pleasing gray color.

The two maximum absorption peaks at 438 nanometers and at 530 nanometers indicate that the recrystallized reaction product of Step 2 consists of at least two structural isomers of the photochromic compound. When the recrystallized reaction product of Step 2 was dissolved in chloroform and subjected to thin film chromatography, one elution peak was observed for the recrystallized product. The presence of two structural isomers is supported by the thin film chromatography results, which indicate that the photochromic compounds contained in the recrystallized reaction product all have the same molecular weight. Thus, it is believed that the recrystallized reaction product obtained in Step 2 contains the following photochromic compound:

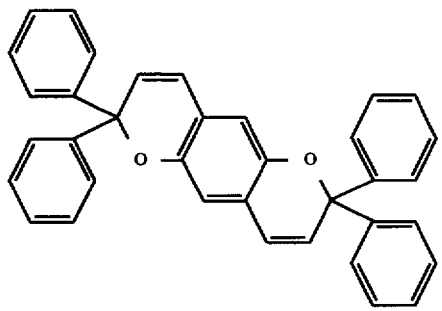

along with at least one photochromic structural isomer of the graphically depicted photochromic compound.

EXAMPLE 2

Step 1

Five grams of 4-benzoylbiphenyl were placed together with five grams of lithium acetylide in 250 milliliters of tetrahydrofuran and stirred for 72 hours. The resultant mixture was poured over ice and diluted with water to form an organic layer and an aqueous layer. The organic layer was separated from the aqueous layer and dried with anhydrous sodium sulfate. The dried organic layer was evaporated to obtain a solid material. The solid material was then triturated with acetone. The triturated material was dissolved in a solvent and the solvent solution was cooled to yield a recrystallized compound. Nuclear magnetic resonance (NMR) spectroscopy showed the resultant material to be a relatively pure propargyl alcohol.

Step 2

Two grams of the propargyl alcohol obtained in Step 1 were mixed with 1.00 grams of hydroquinone in 200 milliliters of benzene. Twenty milligrams of p-toluenesulfonic acid were then added and the mixture was stirred under reflux for 8 hours. The resultant mixture was cooled and washed with 10% aqueous sodium hydroxide. The organic solvent (benzene) was removed using a rotary evaporator. The resulting material was dissolved in hexane and the resulting hexane solution was cooled to yield a recrystallized reaction product. The recrystallized reaction product was shown by nuclear magnetic resonance (NMR) spectroscopy to contain the following photochromic compound:

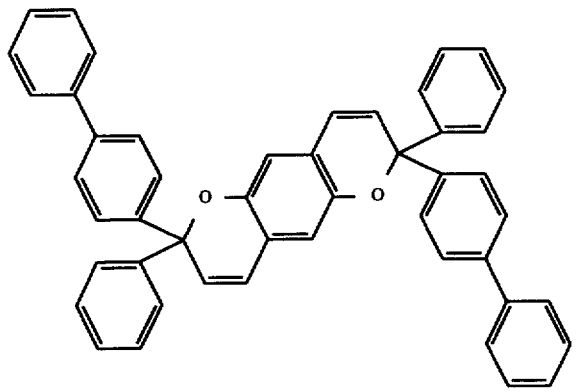

It is also believed that the recrystallized reaction product of Step 2 also contained at least one photochromic structural isomer of this photochromic compound. Ultraviolet visible spectroscopy indicated that the recrystallized reaction product of Step 2, when dissolved in chloroform and irradiated with ultraviolet light of 350 nanometer wavelength, had two maximum wavelengths of absorption at 448 nanometers and at 534 nanometers. Additionally, the irradiated product had a visually pleasing gray color.

The two maximum absorption peaks at 448 nanometers and at 534 nanometers indicate that the recrystallized reaction product of Step 2 consists of at least two structural isomers of the photochromic compound. When the recrystallized reaction product of Step 2 was dissolved in chloroform and subjected to thin film chromatography, one elution peak was observed for the recrystallized reaction product. The presence of two structural isomers is supported by the thin film chromatography results, which indicate that the photochromic compounds contained in the recrystallized reaction product all have the same molecular weight. Thus, it is believed that the recrystallized reaction product obtained in Step 2 contains the following photochromic compound:

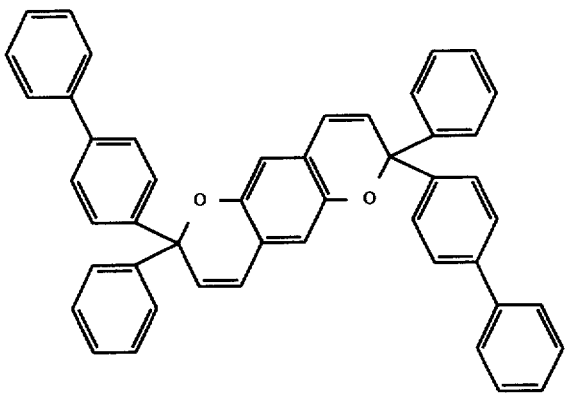

along with at least one photochromic structural isomer of the graphically depicted photochromic compound.

EXAMPLE 3

Step 1

Five grams of 3,4-dimethylbenzophenone were placed together with five grams of lithium acetylide in 250 milliliters of tetrahydrofuran and stirred for 72 hours. The resultant mixture was poured over ice and diluted with water to form an organic layer and an aqueous layer. The organic layer was separated from the aqueous layer and dried with anhydrous sodium sulfate. The dried organic layer was evaporated to obtain a solid material. The solid material was then triturated with acetone. The triturated material was dissolved in a solvent and the solvent solution was cooled to yield a recrystallized compound. Nuclear magnetic resonance (NMR) spectroscopy showed the resultant material to be a relatively pure propargyl alcohol.

Step 2

4.2 grams of the propargyl alcohol obtained in Step 1 were mixed with 1.1 grams of hydroquinone in 200 milliliters of benzene. Twenty milligrams of p-toluenesulfonic acid were then added and the mixture was stirred under reflux for 8 hours. The resultant mixture was cooled and washed with 10% aqueous sodium hydroxide. The organic solvent (benzene) was removed using a rotary evaporator. The resulting material was dissolved in hexane and the resulting hexane solution was cooled to yield a recrystallized reaction product. The recrystallized product was shown by nuclear magnetic resonance (NMR) spectroscopy to contain the following photochromic compound:

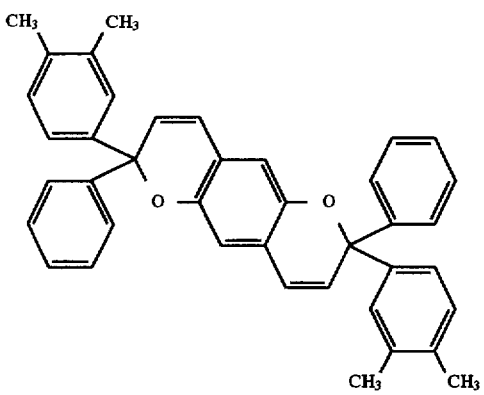

It is also believed that the recrystallized reaction product of Step 2 also contained at least one photochromic structural isomer of this photochromic compound. Ultraviolet visible spectroscopy indicated that the recrystallized reaction product of Step 2, when dissolved in chloroform and irradiated with ultraviolet light of 350 nanometer wavelength, had two maximum wavelengths of absorption at 450 nanometers and at 554 nanometers. Additionally, the irradiated product had a visually pleasing gray color.

The two maximum absorption peaks at 450 nanometers and at 554 nanometers indicate that the recrystallized reaction product of Step 2 consists of at least two structural isomers of the photochromic compound. When the recrystallized reaction product of Step 2 was dissolved in chloroform and subjected to thin film chromatography, one elution peak was observed for the recrystallized reaction product. The presence of two structural isomers is supported by the thin film chromatography results, which indicate that the photochromic compounds contained in the recrystallized reaction product all have the same molecular weight. Thus, it is believed that the recrystallized reaction product obtained in Step 2 contains the following photochromic compound:

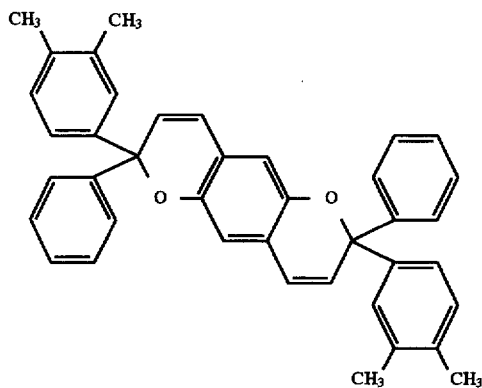

along with at least one photochromic structural isomer of the graphically depicted photochromic compound.

EXAMPLE 4

Step 1

Five grams of 3-chlorobenzophenone were placed together with five grams of lithium acetylide in 250 milliliters of tetrahydrofuran and stirred for 72 hours. The resultant mixture was poured over ice and diluted with water to form an organic layer and an aqueous layer. The organic layer was separated from the aqueous layer and dried with anhydrous sodium sulfate. The dried organic layer was evaporated to obtain a solid material. The solid material was then triturated with acetone. The triturated material was dissolved in a solvent and the solvent solution was cooled to yield a recrystallized compound. Nuclear magnetic resonance (NMR) spectroscopy showed the resultant material to be a relatively pure propargyl alcohol.

Step 2

4.4 grams of the propargyl alcohol obtained in Step 1 were mixed with 1.1 grams of hydroquinone in 200 milliliters of benzene. Twenty milligrams of p-toluenesulfonic acid were then added and the mixture was stirred under reflux for 8 hours. The resultant mixture was cooled and washed with 10% aqueous sodium hydroxide. The organic solvent (benzene) was removed using a rotary evaporator. The resulting material was dissolved in hexane and the resulting hexane solution was cooled to yield a recrystallized reaction product. The recrystallized product was shown by nuclear magnetic resonance (NMR) spectroscopy to contain the following photochromic compound:

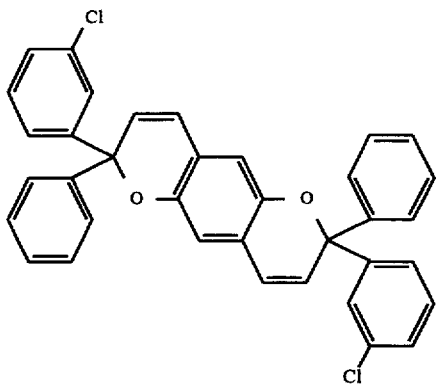

It is also believed that the recrystallized reaction product of Step 2 also contained at least one photochromic structural isomer of this photochromic compound. Ultraviolet visible spectroscopy indicated that the recrystallized reaction product of Step 2, when dissolved in chloroform and irradiated with ultraviolet light of nanometer wavelength, had two maximum wavelengths of absorption at 440 nanometers and at 522 nanometers. Additionally, the irradiated product had a visually pleasing gray color.

The two maximum absorption peaks at 440 nanometers and at 522 nanometers indicate that the recrystallized reaction product of Step 2 consists of at least two structural isomers of the photochromic compound. When the recrystallized reaction product of Step 2 was dissolved in chloroform and subjected to thin film chromatography, one elution peak was observed for the recrystallized reaction product. The presence of two structural isomers is supported by the thin film chromatography results, which indicate that the photochromic compounds contained in the recrystallized reaction product all have the same molecular weight. Thus, it is believed that the recrystallized reaction product obtained in Step 2 contains the following photochromic compound:

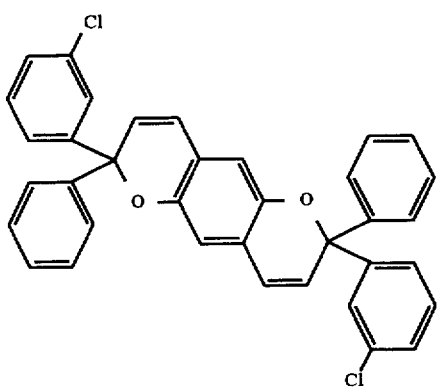

along with at least one photochromic structural isomer of the graphically depicted photochromic compound.

EXAMPLE 5

Step 1

Five grams of 4,4'-dimethoxybenzophenone were placed together with five grams of lithium acetylide in 250 milliliters of tetrahydrofuran and stirred for 72 hours. The resultant mixture was poured over ice and diluted with water to form an organic layer and an aqueous layer. The organic layer was separated from the aqueous layer and dried with anhydrous sodium sulfate. The dried organic layer was evaporated to obtain a solid material. The solid material was then triturated with acetone. The triturated material was dissolved in a solvent and the solvent solution was cooled to yield a recrystallized compound. Nuclear magnetic resonance (NMR) spectroscopy showed the resultant material to be a relatively pure propargyl alcohol.

Step 2

4.8 grams of the propargyl alcohol obtained in Step 1 were mixed with 1.1 grams of hydroquinone in 200 milliliters of benzene. Twenty milligrams of p-toluenesulfonic acid were then added and the mixture was stirred under reflux for 8 hours. The resultant mixture was cooled and washed with 10% aqueous sodium hydroxide. The organic solvent (benzene) was removed using a rotary evaporator. The resulting material was dissolved in hexane and the resulting hexane solution was cooled to yield a recrystallized reaction product. The recrystallized product was shown by nuclear magnetic resonance (NMR) spectroscopy to contain the following photochromic compound:

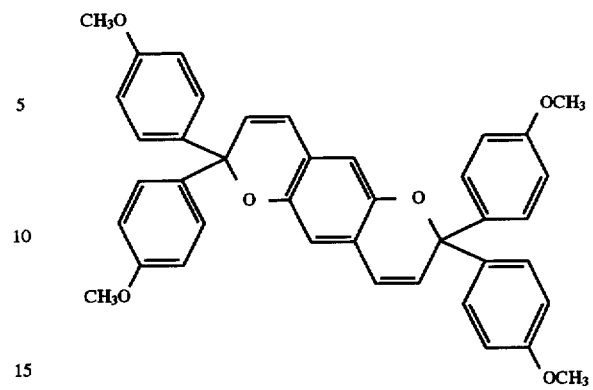

It is also believed that the recrystallized reaction product of Step 2 also contained at least one photochromic structural isomer of this photochromic compound. Ultraviolet visible spectroscopy indicated that the recrystallized reaction product of Step 2, when dissolved in chloroform and irradiated with ultraviolet light of 350 nanometer wavelength, had two maximum wavelengths of absorption at 462 nanometers and at 560 nanometers. Additionally, the irradiated product had a visually pleasing gray color.

The two maximum absorption peaks at 462 nanometers and at 560 nanometers indicate that the recrystallized reaction product of Step 2 consists of at least two structural isomers of the photochromic compound. When the recrystallized reaction product of Step 2 was dissolved in chloroform and subjected to thin film chromatography, one elution peak was observed for the recrystallized reaction product. The presence of two structural isomers is supported by the thin film chromatography results, which indicate that the photochromic compounds contained in the recrystallized reaction product all have the same molecular weight. Thus, it is believed that the recrystallized reaction product obtained in Step 2 contains the following photochromic compound:

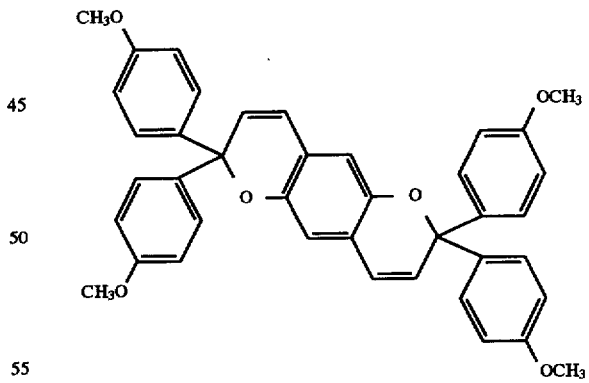

along with at least one photochromic structural isomer of the graphically depicted photochromic compound.

EXAMPLE 6

Step 1

Five grams of 4-methylbenzophenone were placed together with five grams of lithium acetylide in 250 milliliters of tetrahydrofuran and stirred for 72 hours. The resultant mixture was poured over ice and diluted with water to form an organic layer and an aqueous layer. The organic layer was separated from the aqueous layer and dried with anhydrous sodium sulfate. The dried organic layer was evaporated to obtain a solid material. The solid material was then triturated with acetone. The triturated material was dissolved in a solvent and the solvent solution was cooled to yield a recrystallized compound. Nuclear magnetic resonance (NMR) spectroscopy showed the resultant material to be a relatively pure propargyl alcohol.

Step 2

Four grams of the propargyl alcohol obtained in Step 1 were mixed with 1.1 grams of hydroquinone in 200 milliliters of benzene. Twenty milligrams of p-toluenesulfonic acid were then added and the mixture was stirred under reflux for 8 hours. The resultant mixture was cooled and washed with 10% aqueous sodium hydroxide. The organic solvent (benzene) was removed using a rotary evaporator. The resulting material was dissolved in hexane and the resulting hexane solution was cooled to yield a recrystallized reaction product. The recrystallized product was shown by nuclear magnetic resonance (NMR) spectroscopy to contain the following photochromic compound:

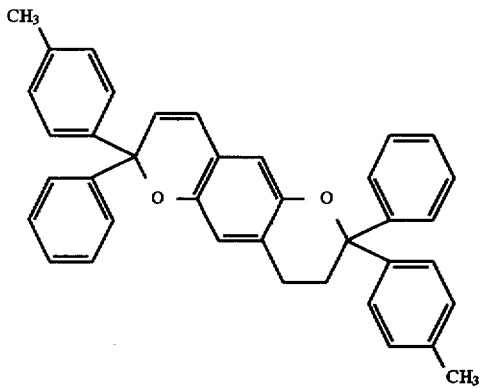

It is also believed that the recrystallized reaction product of Step 2 also contained at least one photochromic structural isomer of this photochromic compound. Ultraviolet visible spectroscopy indicated that the recrystallized reaction product of Step 2, when dissolved in chloroform and irradiated with ultraviolet light of 350 nanometer wavelength, had two maximum wavelengths of absorption at 450 nanometers and at 545 nanometers. Additionally, the irradiated product had a visually pleasing gray color.

The two maximum absorption peaks at 450 nanometers and at 545 nanometers indicate that the recrystallized reaction product of Step 2 consists of at least two structural isomers of the photochromic compound. When the recrystallized reaction product of Step 2 was dissolved in chloroform and subjected to thin film chromatography, one elution peak was observed for the recrystallized reaction product. The presence of two structural isomers is supported by the thin film chromatography results, which indicate that the photochromic compounds contained in the recrystallized reaction product all have the same molecular weight. Thus, it is believed that the recrystallized reaction product obtained in Step 2 contains the following photochromic compound:

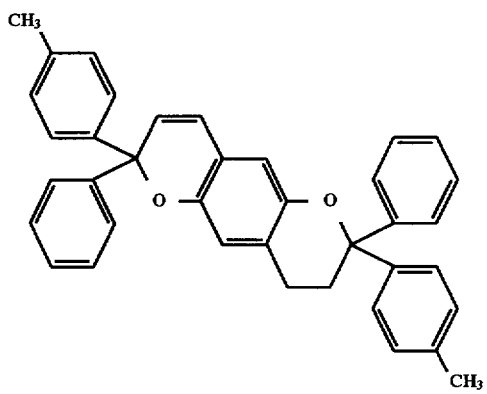

along with at least one photochromic structural isomer of the graphically depicted photochromic compound.

EXAMPLE 7

Step 1

Five grams of benzophenone were placed together with five grams of lithium acetylide in 250 milliliters of tetrahydrofuran and stirred for 72 hours. The resultant mixture was poured over ice and diluted with water to form an organic layer and an aqueous layer. The organic layer was separated from the aqueous layer and dried with anhydrous sodium sulfate. The dried organic layer was evaporated to obtain a solid material. The solid material was then triturated with acetone. The triturated material was dissolved in a solvent and the solvent solution was cooled to yield a recrystallized compound. Nuclear magnetic resonance (NMR) spectroscopy showed the resultant material to be a relatively pure propargyl alcohol.

Step 2

Two grams of the propargyl alcohol obtained in Step 1 were mixed with 1.23 grams of methylhydroquinone in 200 milliliters of benzene. Twenty milligrams of p-toluenesulfonic acid were then added and the mixture was stirred under reflux for 8 hours. The resultant mixture was cooled and washed with 10% aqueous sodium hydroxide. The organic solvent (benzene) was removed using a rotary evaporator. The resulting material was dissolved in hexane and the resulting hexane solution was cooled to yield a recrystallized reaction product. The recrystallized product was shown by nuclear magnetic resonance (NMR) spectroscopy to contain the following photochromic compound:

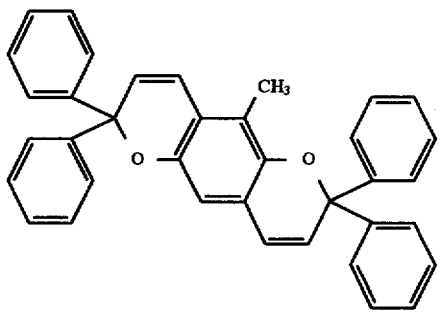

It is also believed that the recrystallized reaction product of Step 2 also contained at least one photochromic structural isomer of this photochromic compound. Ultraviolet visible spectroscopy indicated that the recrystallized reaction product of Step 2, when dissolved in chloroform and irradiated with ultraviolet light of 350 nanometer wavelength, had two maximum wavelengths of absorption at 438 nanometers and at 522 nanometers. Additionally, the irradiated product had a visually pleasing gray color.

The two maximum absorption peaks at 438 nanometers and at 522 nanometers indicate that the recrystallized reaction product of Step 2 consists of at least two structural isomers of the photochromic compound. When the recrystallized reaction product of Step 2 was dissolved in chloroform and subjected to thin film chromatography, one elution peak was observed for the recrystallized reaction product. The presence of two structural isomers is supported by the thin film chromatography results, which indicate that the photochromic compounds contained in the recrystallized reaction product all have the same molecular weight. Thus, it is believed that the recrystallized reaction product obtained in Step 2 contains the following photochromic compound:

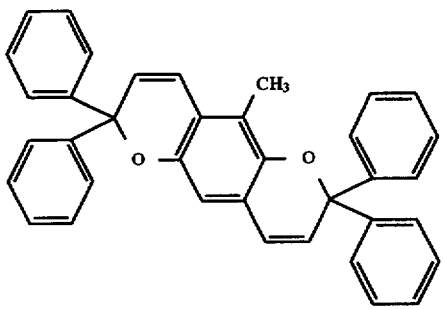

along with at least one photochromic structural isomer of the graphically depicted photochromic compound.

EXAMPLE 8

Step 1

Five grams of benzophenone were placed together with five grams of lithium acetylide in 250 milliliters of tetrahydrofuran and stirred for 72 hours. The resultant mixture was poured over ice and diluted with water to form an organic layer and an aqueous layer. The organic layer was separated from the aqueous layer and dried with anhydrous sodium sulfate. The dried organic layer was evaporated to obtain a solid material. The solid material was then triturated with acetone. The triturated material was dissolved in a solvent and the solvent solution was cooled to yield a recrystallized compound. Nuclear magnetic resonance (NMR) spectroscopy showed the resultant material to be a relatively pure propargyl alcohol.

Step 2

3.6 grams of the propargyl alcohol obtained in Step 1 were mixed with 1.9 grams of phenylhydroquinone in 200 milliliters of benzene. Twenty milligrams of p-toluenesulfonic acid were then added and the mixture was stirred under reflux for 8 hours. The resultant mixture was cooled and washed with 10% aqueous sodium hydroxide. The organic solvent (benzene) was removed using a rotary evaporator. The resulting material was dissolved in hexane and the resulting hexane solution was cooled to yield a recrystallized reaction product. The recrystallized product was shown by nuclear magnetic resonance (NMR) spectroscopy to contain the following photochromic compound:

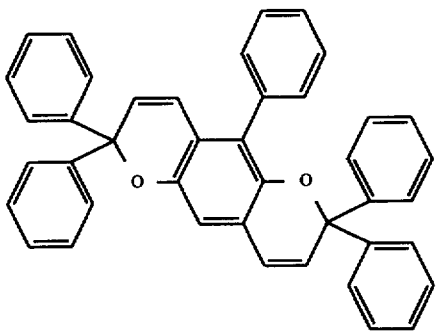

It is also believed that the recrystallized reaction product of Step 2 also contained at least one photochromic structural isomer of this photochromic compound. Ultraviolet visible spectroscopy indicated that the recrystallized reaction product of Step 2, when dissolved in chloroform and irradiated with ultraviolet light of 350 nanometer wavelength, had two maximum wavelengths of absorption at 430 nanometers and at 556 nanometers. Additionally, the irradiated product had a visually pleasing gray color.

The two maximum absorption peaks at 430 nanometers and at 556 nanometers indicate that the recrystallized reaction product of Step 2 consists of at least two structural isomers of the photochromic compound. When the recrystallized reaction product of Step 2 was dissolved in chloroform and subjected to thin film chromatography, one elution peak was observed for the recrystallized reaction product. The presence of two structural isomers is supported by the thin film chromatography results, which indicate that the photochromic compounds contained in the recrystallized reaction product all have the same molecular weight. Thus, it is believed that the recrystallized reaction product obtained in Step 2 contains the following photochromic compound:

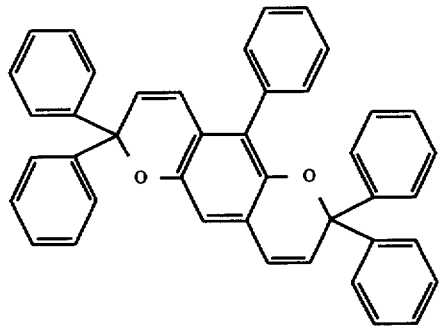

along with at least one photochromic structural isomer of the graphically depicted photochromic compound.

COMPARATIVE EXAMPLE 1

Step 1

Five grams of benzophenone were placed together with 5 grams of lithium acetylide in 250 milliliters of tetrahydrofuran and stirred for 72 hours. The resultant mixture was poured over ice and diluted with water to form an organic layer and an aqueous layer. The organic layer was separated from the aqueous layer and dried with anhydrous sodium sulfate. The dried organic material was evaporated to obtain a solid material. The solid material was triturated with acetone. Nuclear magnetic resonance (NMR) spectroscopy showed the resultant material to be a relatively pure diphenyl propargyl alcohol.

Step 2

Two grams of the diphenyl propargyl alcohol obtained in Step 2 were mixed with 1.71 grams of 6-methoxy-2-naphthol in 200 milliliters of benzene. Twenty milligrams of p-toluenesulfonic acid were then added and the mixture was stirred under reflux for 8 hours. The resultant mixture was cooled and washed with 10% aqueous sodium hydroxide. The organic solvent (benzene) was removed using a rotary evaporator. The resulting material was dissolved in hexane and the resultant hexane solution was cooled to yield a recrystallized product. The recrystallized product was shown to be relatively pure 3,3-diphenyl-8-methoxy-3H-naphtho[2,1b]pyran by nuclear magnetic resonance NMR spectroscopy.

The recrystallized reaction products formed in Steps 2 of Examples 1, 2, 3, 4, 5, 6, 7, and 8; the 3,3-diphenyl-8-methoxy-3H-naphtho[2,1b]pyran formed in Comparative Example 1; and a purchased sample of 3,3-diphenyl-3H-naphtho-[2,1b]pyran (identified as Comparative Example 2) were each individually dissolved in chloroform in separate containers. These chloroform dissolved substances were then irradiated with ultraviolet light having a maximum wavelength of 350 manometers, at room temperature (72° F.), and measured for maximum absorption wavelength, $\lambda_{max}$. The fade time, $T_{1/2}$, was then determined for each of the irradiated substances. The fade time for the chloroform-dissolved substances is defined as the time interval, at room temperature (72° F.), for the absorbance of the activated form of each chloroform-dissolved substance to decrease to one half of the maximum absorbance, after the substance is isolated from the activating source of ultraviolet light. The maximum absorption wavelength and fade time determined for the irradiated substances of Examples 1-8 and Comparative Examples 1-2 are presented in Table 1:

TABLE 1

| SOLVENT | $\lambda_{max}$ [nanometers] Chloroform | $T_{1/2}$ [seconds] Chloroform |
|---|---|---|
| EXAMPLE | | |
| 1 | 438 & 530 | 8 |
| 2 | 448 & 534 | 20 |
| 3 | 450 & 554 | 16.5 |
| 4 | 440 & 522 | 23 |
| 5 | 462 & 560 | 7 |
| 6 | 450 & 545 | 24 |
| 7 | 438 & 522 | 18.5 |
| 8 | 430 & 556 | |
| COMPARATIVE EXAMPLE | | |
| 1 | 472 | 10 |
| 2 | 434 | 13 |

Comparative Example 2: Purchased 3,3-diphenyl-3H-naphtho-[2,1b]pyran

The values presented in Table 1 illustrate that the inventive photochromic reaction products of Examples 1-8 each have a pair of maximum wavelengths of activation, as compared to the 3,3-diphenyl-8-methoxy-3H-naphtho[2,1b] pyran of Comparative Example 1 and the 3,3-diphenyl-3H-naphtho-[2,1b]pyran of Comparative Example 2, which each have only a single maximum wavelength of activation. This combination of longer and shorter maximum wavelengths of activation for the inventive photochromic reaction products is a desirable characteristic for photochromic compositions, since gray-turning photochromic mixtures may be prepared in one reaction sequence without having to later blend photochromic compounds having different maximum activated wavelengths of absorption.

Also, one of the maximum wavelengths of activation of each of the inventive photochromic reaction products of Examples 1-8 is longer than the single maximum wavelength of activation of the 3,3-diphenyl-8-methoxy-3H-naphtho [2,1b]pyran of Comparative Example 1 and the 3,3-diphenyl-3H-naphtho-[2,1b]pyran of Comparative Example 2. Furthermore, the fade times, $T_{1/2}$, of the inventive photochromic reaction products of Examples 1-7 range from seven (7) to twenty-four (24) seconds, which are within the range of desirable fade times for photochromic compositions.

Besides the desirable maximum absorption wavelengths, the inventive photochromic compounds of Examples 1-8 have other desirable photochromic characteristics. For example, the inventive photochromic compounds have desirable activated coloring attributes, such as the hue, lightness, and saturation of the color each individual compound changes to. Also, the inventive photochromic compounds of Examples 1-8 change from the original color state to the activated color at desirable rates when exposed to ultraviolet light. Additionally, when activated by ultraviolet light, the aforementioned desirable coloring characteristics are stable and are not deleteriously affected by light having wavelengths different from the wavelength of the activating source. Furthermore, each inventive photochromic compound and photochromic reaction mixture of Examples 1-8 has a distinct set of definitive photochromic characteristics that lends to flexible use of each of the inventive photochromic compounds and reaction mixtures in particular photochromic applications, as compared to existing photochromic compounds and compositions.

Although the present invention has been described with reference to preferred embodiments, workers smiled in the art will recognize that changes may be made in form and detail without departing from the spirit and scope of the invention.

What is claimed is:

1. A photochromic compound, or a structural isomer of the photochromic compound, the photochromic compound represented by the formula:

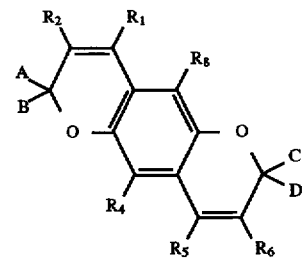

wherein $R_1$, $R_2$, $R_4$, $R_5$, $R_6$, $R_8$, A, B, C, and D are each individually selected from the group consisting of hydrogen, alkyl, alkoxy, phenyl, naphthyl, cycloalkyl, furyl, alkoyl, alkoyloxy, aroyl, aroyloxy, halogen, amino, dialkyl amino, nitro, morpholino, piperidino, and piperazino, provided that at least one of A, B, C, or D is selected from the group consisting of alkoxy, phenyl, naphthyl, cycloalkyl, furyl, alkoyl, alkoyloxy, aroyl, aroyloxy, halogen, amino, dialkyl amino, nitro, morpholino, piperidino, and piperazino.

2. A photochromic compound, or a structural isomer of the photochromic compound, the photochromic compound represented by the formula:

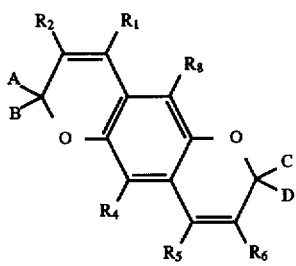

wherein $R_1$, $R_2$, $R_4$, $R_5$, $R_6$, $R_8$, A, B, C, and D are each individually selected from the group consisting of hydrogen, alkyl, alkoxy, phenyl, naphthyl, cycloalkyl, furyl, alkoyl, alkoyloxy, aroyl, aroyloxy, halogen, amino, dialkyl amino, nitro, morpholino, piperidino, and piperazino, provided that at least $R_4$ or $R_8$ is selected from the group consisting of alkoxy, phenyl, naphthyl, cycloalkyl, furyl, alkoyl, alkoyloxy, aroyl, aroyloxy, halogen, amino, dialkyl amino, nitro, morpholino, piperidino, and piperazino.

3. A photochromic compound or a structural isomer of the photochromic compound, the photochromic compound represented by the formula:

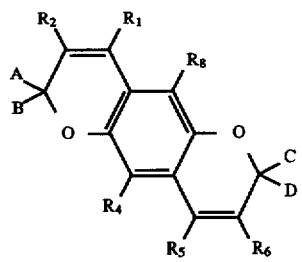

wherein $R_1$, $R_2$, $R_4$ $R_5$ $R_6$ $R_8$, A, B, C, and D are each individually selected from the group consisting of hydrogen, alkyl, alkoxy, phenyl, naphthyl, cycloalkyl, furyl, alkoyl, alkoyloxy, aroyl, aroyloxy, halogen, amino, dialkyl amino, nitro, morpholino, piperidino, and piperazino, provided that $R_4$ and $R_8$ are different from each other.

4. A photochromic compound, or a structural isomer of the photochromic compound, the photochromic compound represented by the formula:

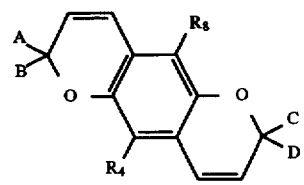

wherein $R_4$, $R_8$, A, B, C, and D are each individually selected from the group consisting of hydrogen, alkyl, alkoxy, phenyl, naphthyl, cycloalkyl, furyl, alkoyl, alkoyloxy, aroyl, aroyloxy, halogen, amino, dialkyl amino, nitro, morpholino, piperidino, and piperazino, provided that at least one of A, B, C, or D is selected from the group consisting of alkoxy, phenyl, naphthyl, cycloalkyl, furyl, alkoyl, alkoyloxy, aroyl, aroyloxy, halogen, amino, dialkyl amino, nitro, morpholino, piperidino, and piperazino.

5. A photochromic compound, or a structural isomer of the photochromic compound, the photochromic compound represented by the formula:

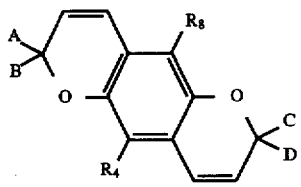

wherein $R_4$, $R_8$, A, B, C, and D are each individually selected from the group consisting of hydrogen, alkyl, alkoxy, phenyl, naphthyl, cycloalkyl, furyl, alkoyl, alkoyloxy, aroyl, aroyloxy, halogen, amino, dialkyl amino, nitro, morpholino, piperidino, and piperazino, provided that at least $R_4$ or $R_8$ is selected from fie group consisting of alkoxy, phenyl, naphthyl, cycloalkyl, furyl, alkoyl, alkoyloxy, aroyl, aroyloxy, halogen, amino, dialkyl amino, nitro, morpholino, piperidino, and piperazino.

6. A photochromic compound, or a structural isomer of the photochromic compound, the photochromic compound represented by the formula:

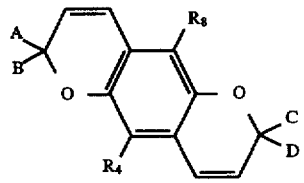

wherein $R_4$, $R_8$, A, B, C, and D are each individually selected from the group consisting of hydrogen, alkyl, alkoxy, phenyl, naphthyl, cycloalkyl, furyl, alkoyl, alkoyloxy, aroyl, aroyloxy, halogen, amino, dialkyl amino, nitro, morpholino, piperidino, and piperazino, provided that $R_4$ and $R_8$ are different from each other.

7. A photochromic compound, or a structural isomer of the photochromic compound, the photochromic compound represented by the formula:

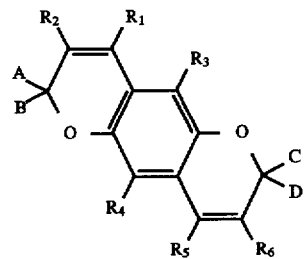

wherein $R_1$, $R_2$, $R_4$, $R_5$, $R_6$, and $R_8$ are each individually selected from group consisting of hydrogen, alkyl, alkoxy, phenyl, naphthyl, cycloalkyl, furyl, alkoyl, alkoyloxy, aroyl, aroyloxy, halogen, amino, dialkyl amino, nitro, morpholino, piperidino, and piperazino; and
wherein A, B, C, and D are each individually selected from the group consisting of an unsubstituted monovalent aromatic group and a substituted monovalent aromatic group, the substituents of the substituted monovalent aromatic group selected from the group consisting of alkyl, alkoxy, phenyl, naphthyl, cycloalkyl, furyl, alkoyl, alkoyloxy, aroyl, aroyloxy, halogen, amino, dialkyl amino, nitro, morpholino, piperidino, and piperazino.

8. A photochromic compound, or a structural isomer of the photochromic compound, the photochromic compound represented by the formula:

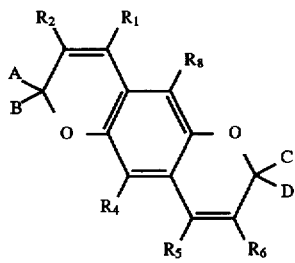

wherein $R_1$, $R_2$, $R_4$, $R_5$, $R_6$, and $R_8$, are each individually selected from the group consisting of hydrogen, alkyl, alkoxy, phenyl, naphthyl, cycloalkyl, furyl, alkoyl, alkoyloxy, aroyl, aroyloxy, halogen, amino, dialkyl amino, nitro, morpholino, piperidino, and piperazino, provided that at least $R_4$ or $R_8$ is selected from the group consisting of alkoxy, phenyl, naphthyl, cycloalkyl, furyl, alkoyl, alkoyloxy, aroyl, aroyloxy, halogen, amino, dialkyl amino, nitro, morpholino, piperidino, and piperazino; and wherein A, B, C, and D are each individually selected from the group consisting of an unsubstituted monovalent aromatic group and a substituted monovalent aromatic group, the substituents of the substituted monovalent aromatic group selected from the group consisting of alkyl, alkoxy, phenyl, naphthyl, cycloalkyl, furyl, alkoyl, alkoyloxy, aroyl, aroyloxy, halogen, amino, dialkyl amino, nitro, morpholino, piperidino, and piperazino.

9. A photochromic compound, or a structural isomer of the photochromic compound, the photochromic compound represented by the formula:

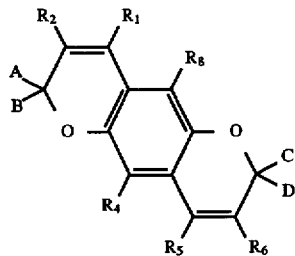

wherein $R_1$, $R_2$, $R_4$, $R_5$, $R_6$, and $R_8$ are each individually selected from the group consisting of hydrogen, alkyl, alkoxy, phenyl, naphthyl, cycloalkyl, furyl, alkoyl, alkoyloxy, aroyl, aroyloxy, halogen, amino, dialkyl amino, nitro, morpholino, piperidino, and piperazino, provided that at least $R_4$ and $R_8$ are different from each other; and wherein A, B, C, and D are each individually selected from the group consisting of an unsubstituted monovalent aromatic group and a substituted monovalent aromatic group, the substituents of the substituted monovalent aromatic group selected from the group consisting of alkyl, alkoxy, phenyl, naphthyl, cycloalkyl, furyl, alkoyl, alkoyloxy, aroyl, aroyloxy, halogen, amino, dialkyl amino, nitro, morpholino, piperidino, and piperazino.

10. A photochromic compound, or a structural isomer of the photochromic compound, the photochromic compound represented by the formula:

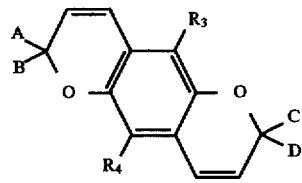

wherein $R_4$ and $R_8$ are each individually selected from the group consisting of hydrogen, alkyl, alkoxy, phenyl, naphthyl, cycloalkyl, furyl, alkoyl, alkoyloxy, aroyl, aroyloxy, halogen, amino, dialkyl amino, nitro, morpholino, piperidino, and piperazino; and wherein A, B, C, and D are each individually selected from the group consisting of an unsubstituted monovalent aromatic group and a substituted monovalent aromatic group, the substituents of the substituted monovalent aromatic group selected from the group consisting of alkyl, alkoxy, phenyl, naphthyl, cycloalkyl, furyl, alkoyl, alkoyloxy, aroyl, aroyloxy, halogen, amino, dialkyl amino, nitro, morpholino, piperidino, and piperazino.

11. A photochromic compound, or a structural isomer of the photochromic compound, the photochromic compound represented by the formula:

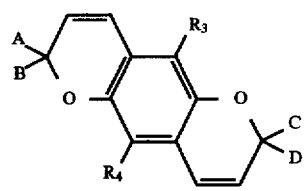

wherein $R_4$ and $R_8$ are each individually selected from the group consisting of hydrogen, alkyl, alkoxy, phenyl, naphthyl, cycloalkyl, furyl, alkoyl, alkoyloxy, aroyl, aroyloxy, halogen, amino, dialkyl amino, nitro, morpholino, piperidino, and piperazino, provided that at least $R_4$ or $R_8$ is selected from the group consisting of alkoxy, phenyl, naphthyl, cycloalkyl, furyl, alkoyl, alkoyloxy, aroyl, aroyloxy, halogen, amino, dialkyl amino, nitro, morpholino, piperidino, and piperazino; and wherein A, B, C, and D are each individually selected from the group consisting of an unsubstituted monovalent aromatic group and a substituted monovalent aromatic group, the substituents of the substituted monovalent aromatic group selected from the group consisting of alkyl, alkoxy, phenyl, naphthyl, cycloalkyl, furyl, alkoyl, alkoyloxy, aroyl, aroyloxy, halogen, amino, dialkyl amino, nitro, morpholino, piperidino, and piperazino.

12. A photochromic compound, or a structural isomer of the photochromic compound, the photochromic compound represented by the formula:

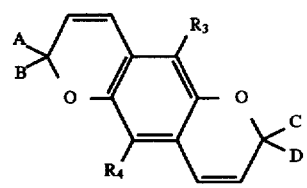

wherein $R_4$ and $R_8$ are each individually selected from the group consisting of hydrogen, alkyl, alkoxy, phenyl, naphthyl, cycloalkyl, furyl, alkoyl, alkoyloxy, aroyl, aroyloxy, halogen, amino, dialkyl amino, nitro, morpholino, piperidino, and piperazino, provided that $R_4$ and $R_8$ are different from each other; and wherein A, B, C, and D am each individually selected from the group consisting of an unsubstituted monovalent aromatic group and a substituted monovalent aromatic group, the substituents of the substituted monovalent aromatic group selected from the group consisting of alkyl, alkoxy, phenyl, naphthyl, cycloalkyl, furyl, alkoyl, alkoyloxy, aroyl, aroyloxy, halogen, amino, dialkyl amino, nitro, morpholino, piperidino, and piperazino.

13. A photochromic composition, the photochromic composition comprising:

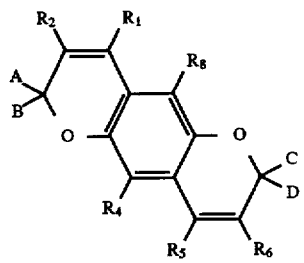

wherein $R_1$, $R_2$, $R_4$, $R_5$, $R_6$, $R_8$, A, B, C, and D are each individually selected from the group consisting of hydrogen, alkyl, alkoxy, phenyl, naphthyl, cycloalkyl, furyl, alkoyl, alkoyloxy, aroyl, aroyloxy, halogen, amino, dialkyl amino, nitro, morpholino, piperidino, and piperazino, provided that at least one of A, B, C, or D is selected from the group consisting of alkoxy, halogen, amino, dialkyl amino, nitro, morpholino, piperidino, and piperazino; and at least one structural isomer of:

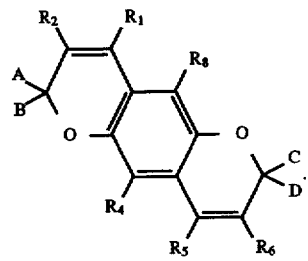

14. A photochromic composition, the photochromic composition comprising:

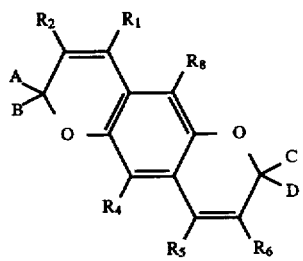

wherein $R_1$, $R_2$, $R_4$, $R_5$, $R_6$, $R_8$, A, B, C, and D are each individually selected from the group consisting, of hydrogen, alkyl, alkoxy, phenyl, naphthyl, cycloalkyl, furyl, alkoyl, alkoyloxy, aroyl, aroyloxy, halogen, amino, dialkyl amino, nitro, morpholino, piperidino, and piperazino, provided that at least $R_4$ or $R_8$ is selected from the group consisting of alkoxy, phenyl, naphthyl, cycloalkyl, furyl, alkoyl, alkoyloxy, aroyl, aroyloxy, halogen, amino, dialkyl amino, nitro, morpholino piperidino, and piperazino; and least one structural isomer of:

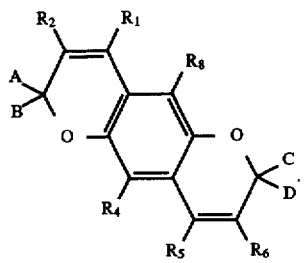

15. A photochromic composition, the photochromic composition comprising:

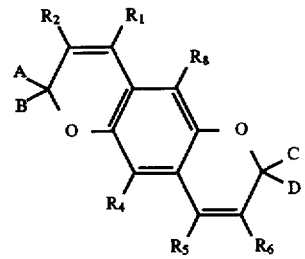

wherein $R_1$, $R_2$, $R_4$, $R_5$, $R_6$, $R_8$, A, B, C, and D are each individually selected from the group consisting of hydrogen, alkyl, alkoxy, phenyl, naphthyl, cycloalkyl, furyl, alkoyl, alkoyloxy, aroyl, aroyloxy, halogen, amino, dialkyl amino, nitro, morpholino, piperidino, and piperazino, provided that $R_4$ and $R_8$ are different from each other; and at least one structural isomer of:

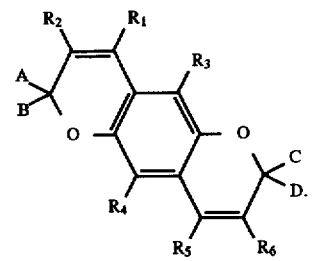

16. A photochromic composition, the photochromic composition comprising:

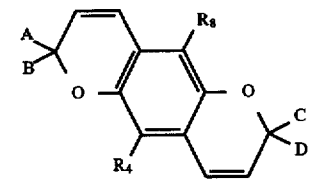

wherein $R_4$, $R_8$, A, B, C, and D are each individually selected from the group consisting of hydrogen, alkyl, alkoxy, phenyl, naphthyl, cycloalkyl, furyl, alkoyl, alkoyloxy, aroyl, aroyloxy, halogen, amino, dialkyl amino, nitro, morpholino, piperidino, and piperazino, provided that at least one of A, B, C, or D is selected from the group consisting of alkoxy, phenyl, naphthyl, cycloalkyl, furyl, alkoyl, alkoyloxy, aroyl, aroyloxy, halogen, amino, dialkyl amino, nitro, morpholino, piperidino, and piperazino; and

29 at least one structural isomer of:

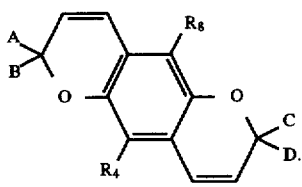

17. A photochromic composition, the photochromic composition comprising:

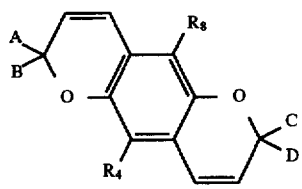

wherein $R_4$, $R_8$, A, B, C, and D are each individually selected from the group consisting of hydrogen, alkyl, alkoxy, phenyl, naphthyl, cycloalkyl, furyl, alkoyl, alkoyloxy, aroyl, aroyloxy, halogen, amino, dialkyl amino, nitro, morpholino, piperidino, and piperazino, provided that at least $R_4$ or $R_8$ is selected from the group consisting of alkoxy, phenyl, naphthyl, cycloalkyl, furyl, alkoyl, alkoyloxy, aroyl, aroyloxy, halogen, amino, dialkyl amino, nitro, morpholino, piperidino, and piperazino; and at least one structural isomer of:

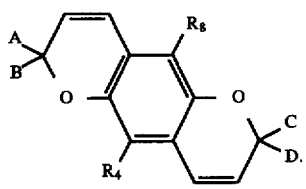

18. A photochromic composition, the photochromic composition comprising:

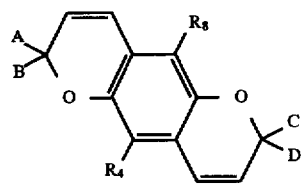

wherein $R_4$, $R_8$, A, B, C, and D are each individually selected from the group consisting of hydrogen, alkyl, alkoxy, phenyl, naphthyl, cycloalkyl, furyl, alkoyl, alkoyloxy, aroyl, aroyloxy, halogen, amino, dialkyl amino, nitro, morpholino, piperidino, and piperazino, provided that $R_4$ and $R_8$ are different from each other; and

30 at least one structural isomer of:

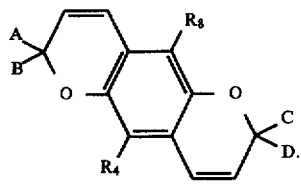

19. A photochromic composition, the photochromic composition comprising:

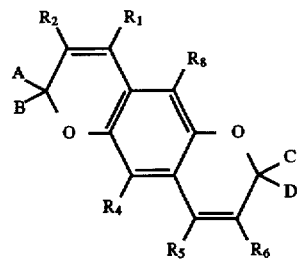

wherein $R_1$, $R_2$, $R_4$, $R_5$, $R_6$, $R_8$ are each individually selected from the group consisting of hydrogen, alkyl, alkoxy, phenyl, naphthyl, cycloalkyl, furyl, alkoyl, alkoyloxy, aroyl, aroyloxy, halogen, amino, dialkyl amino, nitro, morpholino, piperidino, and piperazino; and wherein A, B, C, and D are each individually selected from the group consisting of an unsubstituted monovalent aromatic group and a substituted monovalent aromatic group, the substituents of the substituted monovalent aromatic group selected from the group consisting of alkyl, alkoxy, phenyl, naphthyl, cycloalkyl, furyl, alkoyl, alkoyloxy, aroyl, aroyloxy, halogen, amino, dialkyl amino, nitro, morpholino, piperidino, and piperazino; and at least one structural isomer of:

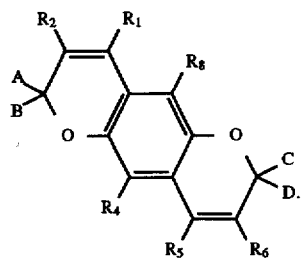

20. A chromene derivative represented by the formula:

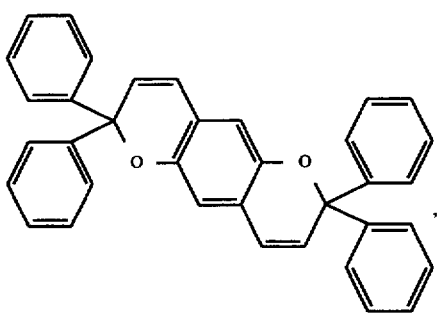

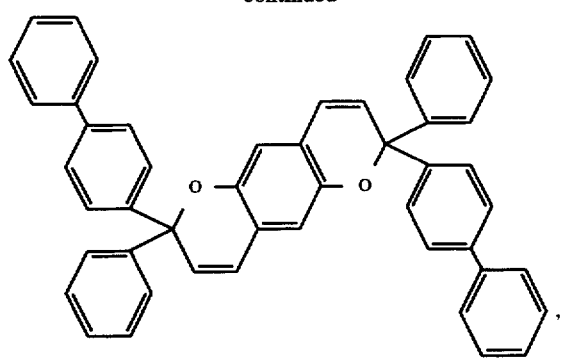
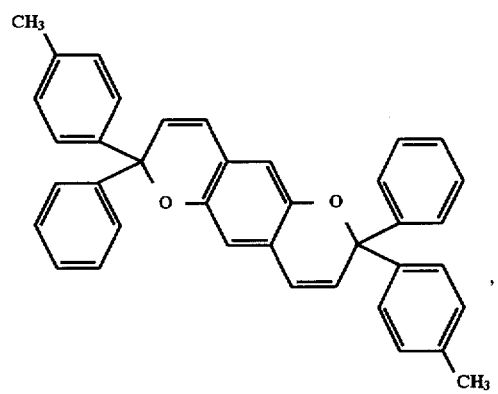
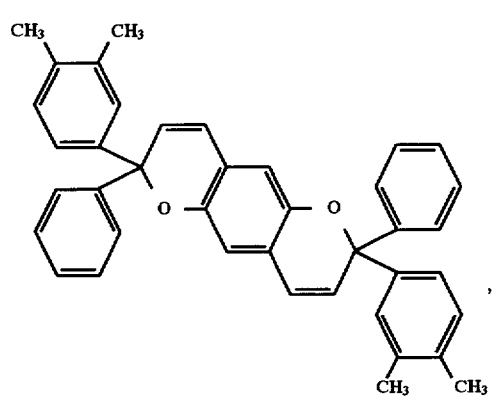
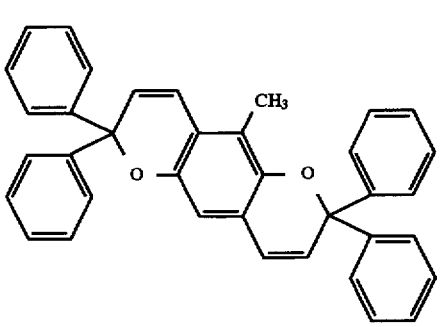
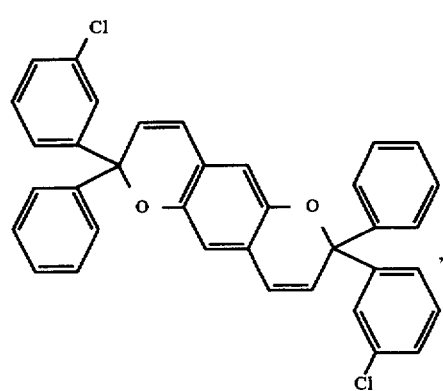
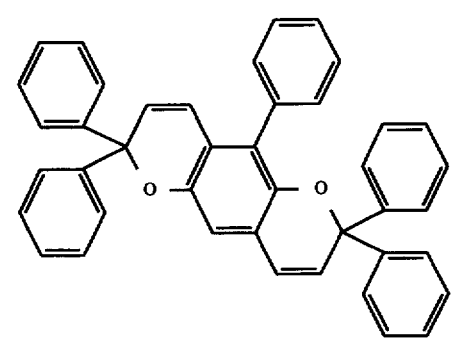
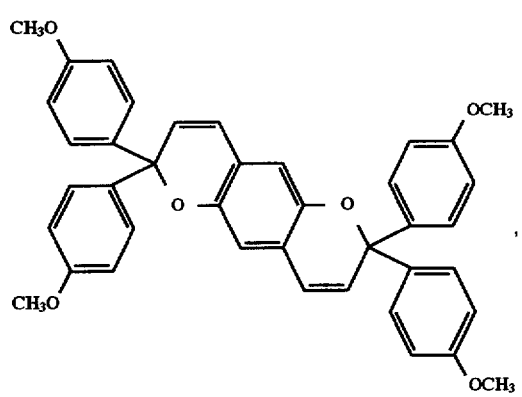
or, a structural isomer of any of these.
* * * * *

UNITED STATES PATENT AND TRADEMARK OFFICE
CERTIFICATE OF CORRECTION

PATENT NO. : 5,702,645
DATED : DECEMBER 30, 1997
INVENTOR(S) : FRANK J. HUGHES

It is certified that error appears in the above-identified patent and that said Letters Patent is hereby corrected as shown below:

Col. 9, line 20, delete "rages", insert --ranges--

Col. 22, line 37, delete "smiled", insert --skilled--

Col. 24, line 15, delete "fie", insert --the--

Col. 24, lines 40-49, delete the following formula:

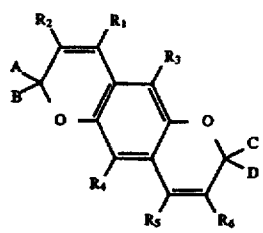

and insert the following formula:

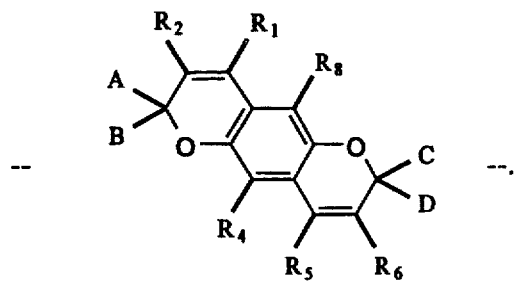

UNITED STATES PATENT AND TRADEMARK OFFICE
CERTIFICATE OF CORRECTION

PATENT NO. : 5,702,645

DATED : DECEMBER 30, 1997

INVENTOR(S) : FRANK J. HUGHES

It is certified that error appears in the above-identified patent and that said Letters Patent is hereby corrected as shown below:

Col. 26, lines 1-9, delete the following formula:

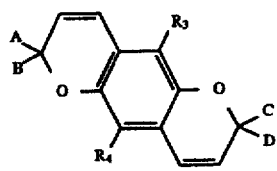

and insert the following formula:

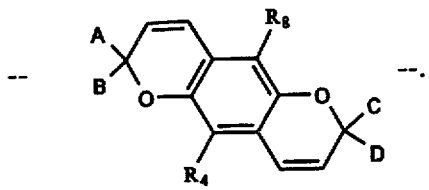

UNITED STATES PATENT AND TRADEMARK OFFICE
CERTIFICATE OF CORRECTION

PATENT NO. : 5,702,645
DATED : DECEMBER 30, 1997
INVENTOR(S) : FRANK J. HUGHES

Page 3 of 6

It is certified that error appears in the above-identified patent and that said Letters Patent is hereby corrected as shown below:

Col. 26, lines 26-34, delete the following formula:

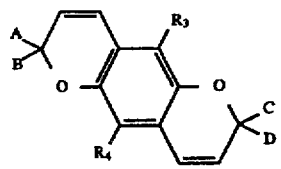

and insert the following formula:

-- 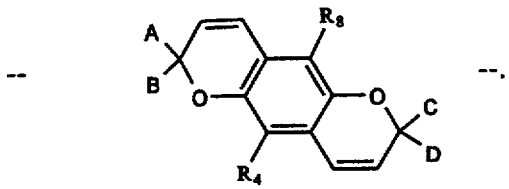 --.

UNITED STATES PATENT AND TRADEMARK OFFICE
CERTIFICATE OF CORRECTION

PATENT NO. : 5,702,645

DATED : DECEMBER 30, 1997

INVENTOR(S) : FRANK J. HUGHES

It is certified that error appears in the above-identified patent and that said Letters Patent is hereby corrected as shown below:

Col. 26, lines 55-64 delete the following formula:

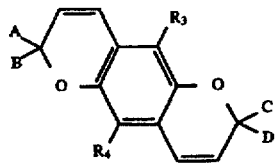

and insert the following formula:

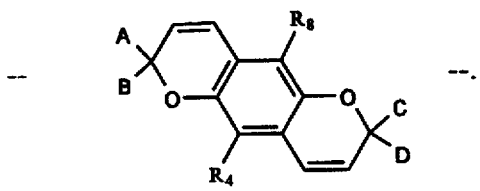

UNITED STATES PATENT AND TRADEMARK OFFICE
CERTIFICATE OF CORRECTION

PATENT NO. : 5,702,645
DATED : DECEMBER 30, 1997
INVENTOR(S) : FRANK J. HUGHES

It is certified that error appears in the above-identified patent and that said Letters Patent is hereby corrected as shown below:

Col. 27, line 3, delete "am", insert --are--

Col. 27, line 30, between "alkoxy", and "halogen," insert --phenyl, naphthyl, cycloalkyl, furyl, alkoyl, alkoyloxy, aroyl, aroyloxy--

Col. 28, lines 35-45, delete the following formula:

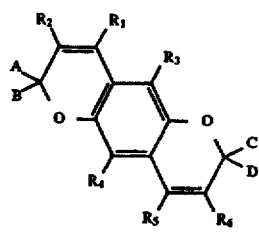

and insert the following formula--

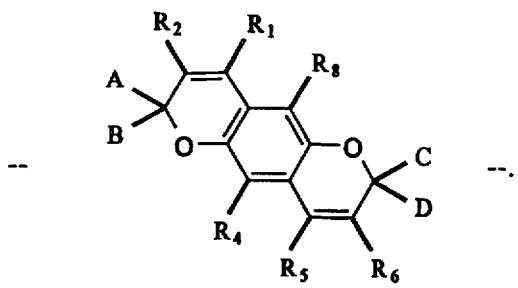

UNITED STATES PATENT AND TRADEMARK OFFICE
CERTIFICATE OF CORRECTION

PATENT NO. : 5,702,645
DATED : DECEMBER 30, 1997
INVENTOR(S) : FRANK J. HUGHES

It is certified that error appears in the above-identified patent and that said Letters Patent is hereby corrected as shown below:

Col. 30, line 25, between "$R_{62}$" and "$R_8$", insert --and--

Signed and Sealed this

Second Day of February, 1999

Attest:

Attesting Officer

*Acting Commissioner of Patents and Trademarks*